United States Patent [19]

Sano et al.

[11] Patent Number: 4,947,837

[45] Date of Patent: Aug. 14, 1990

[54] METHOD OF BLOOD FLOW IMAGING

[75] Inventors: Koichi Sano, Sagamihara; Tetsuo Yokoyama, Tokyo; Hideaki Koizumi, Katsuta, all of Japan

[73] Assignee: Hitachi, Ltd., Tokyo, Japan

[21] Appl. No.: 379,674

[22] Filed: Jul. 13, 1989

Related U.S. Application Data

[63] Continuation of Ser. No. 149,503, Jan. 28, 1988, abandoned.

[30] Foreign Application Priority Data

Jan. 30, 1987 [JP] Japan ................................ 62-18385

[51] Int. Cl.⁵ .............................................. A61B 5/055
[52] U.S. Cl. .............................. 128/653 AF; 324/306; 324/309
[58] Field of Search ................. 128/653; 324/306, 309

[56] References Cited

U.S. PATENT DOCUMENTS

| | | | |
|---|---|---|---|
| 4,516,582 | 5/1985 | Redington | 128/653 |
| 4,528,985 | 7/1985 | Macovski | 128/653 |
| 4,602,641 | 7/1986 | Feinberg | 128/653 |
| 4,683,431 | 7/1987 | Pattany et al. | 128/653 X |
| 4,707,658 | 11/1987 | Frahm et al. | 128/653 |
| 4,727,882 | 3/1988 | Schneider et al. | 128/653 |

Primary Examiner—Ruth S. Smith
Attorney, Agent, or Firm—Antonelli, Terry, Stout & Kraus

[57] ABSTRACT

The blood flow imaging method excites selectively a partial region of the body to be tested including blood vessels inside or outside of the view field of image, measures resonance signals by utilizing spins flowing out of the excited region, and images a blood vessel system based on the blood flow information included in the measured resonance signals. The method images only blood vessels through a single shot of scanning, thereby reducing the time for scanning and enabling the observation of finer vessels.

20 Claims, 5 Drawing Sheets

METHOD OF BLOOD FLOW IMAGING

This application is a Continuation of application Ser. No. 149,503, filed Jan. 28, 1988 now abandoned.

BACKGROUND OF THE INVENTION

This invention relates to a method of tomography utilizing the nuclear magnetic resonance phenomenon and, particularly, to a method of imaging running blood vessels in the body.

A conventional typical method is described in a publication Radiology, May (1986), pp. 411–418. This method uses a sequence for varying the intensity only for blood flows, without affecting static portions, to take two scans so that the intensity varies only in a blood vessel portion, and extracts the blood vessels from the differential image. The principle of the method is that the movement causes spins in the blood vessel to vary in proportion to the velocity, which results in the variation of intensity.

The above-mentioned technique inherently needs to implement the differentiation (subtraction) as mentioned above, and needs to take at least two scans. Therefore, it not only takes a longer time for scanning, but also is incapable of visualizing fine blood vessels due to the displacement between the two scans.

SUMMARY OF THE INVENTION

An object of this invention is to provide a method of extracting blood vessels through a single scanning.

The above objective is accomplished by exciting selectively a part of an image frame, either inside or outside of the view field, and catching spins included in the region moving out of the region. FIGS. 1A and 1B illustrate such a process, and FIG. 3 shows an example of the pulse sequence which carries out the process.

The pulse sequence shown in FIG. 3 will be explained as an example. Gz is a gradient magnetic field with a varying field strength in the z-direction, and Gy and Gx are gradient magnetic fields in the y and x directions, respectively. RF is a highfrequency pulse used for exciting spins in the body. In this example, a static magnetic field is applied in the y-direction. Although Gz is unused in the example of FIG. 3, it is used when the portion to be scanned is changed. Gy is used to determine the view field in the y-direction, to confine the region of spins to be selected, and to separate spin positions in the y-direction. Gx is used to determine the view field in the x-direction and to separate spin positions in the x-direction.

The principle of this invention will be described in detail.

A region 101 in FIG. 1 including a blood vessel 100 in which blood flows in the direction shown by arrow A is excited selectively using a 90°, pulse 301 in FIG. 3. Since spins in a specific region in the y-direction are to be selected, a magnetic field 303 is applied at the same time. Consequently, a magnitude of the magnetic field in the y-direction is varied, so that only the region 101 supplied with a specific magnitude of the magnetic field is excited. At this time, a magnetic field 305 is also applied for the sake of cancelling the variation in phase of spins which move during the signal measurement.

Subsequently, a 180° pulse 302 is applied for the measurement of signals from spins which have been excited selectively. This applying the 180° pulse is intended for eliminating the unevenness of a static magnetic field. In order to measure signals from spins not only in the region with the applying the pulse 301, but also from a moving region, the 180° pulse 302 is made to be a nonselective one and the entire frame including the view field 102 which is the imaging region is excited.

In order to separate spin positions in the y-direction, a phase-encode magnetic field 304 is applied next.

Finally, a gradient magnetic field 306 for reading signals is applied, and signals are read out.

Using the foregoing sequence, only the portion 103 as shown by hatching in FIG. 1B is imaged, and the blood vessel portion 103B is extracted. Namely, the imaged region is only spins that are sensitive to both the 90° pulse and 180° pulse in the view field 102, and only an upper end section 103A and the blood vessel portion 103B within the view field are imaged.

Although in the above explanation, the image selecting direction (y-direction) and the phase-encoding direction (y-direction) are made coincident, it is of course possible to make them opposite and implement imaging by making the image selecting direction and a read-out direction coincident, as shown in FIG. 4.

DESCRIPTION OF THE PREFERRED EMBODIMENTS

Figure 2:
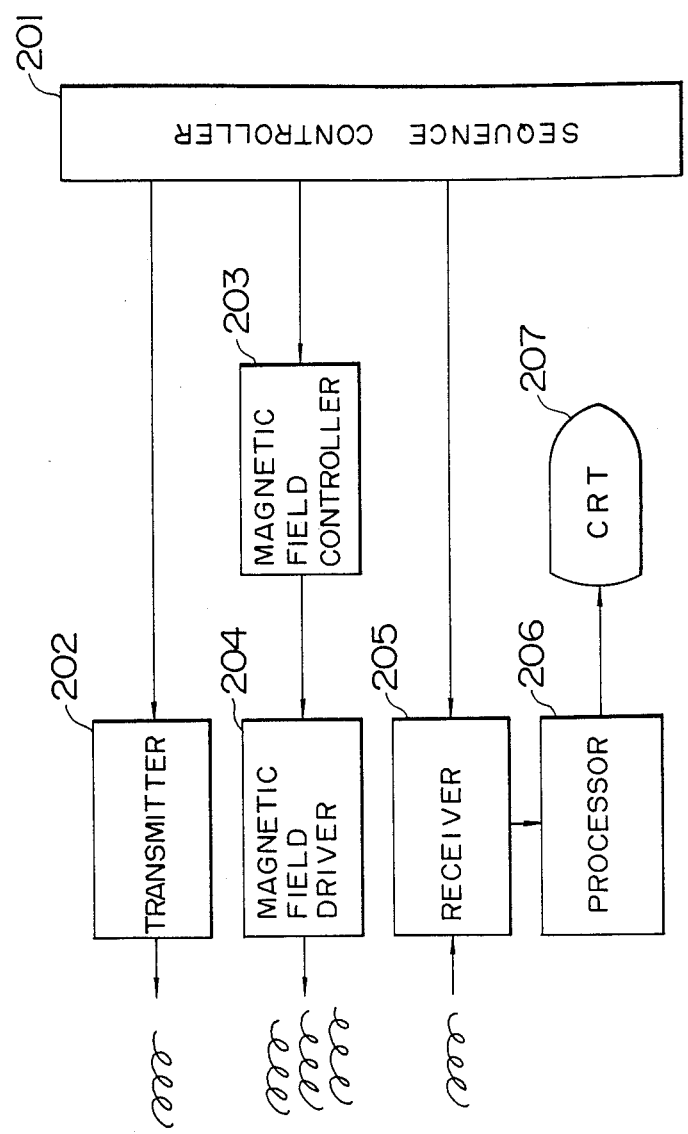
FIG. 2 is a block diagram of the apparatus used for the inventive blood flow imaging method.

Embodiments of this invention will be described in detail. FIG. 2 is a block diagram showing an embodiment of this invention. A sequence controller 201 which controls various pulses and magnetic fields for detecting the NMR signal from the body to be examined controls a transmitter 202 which generates high-frequency (RF) pulses for resonating a specific nuclide in the body, a magnetic field controller 203 which generates a static magnetic field for determining the resonance frequency of the NMR signal and gradient magnetic fields with controllable strengths and directions, and a receiver 205 which detects and measures the NMR signal released from the body. Based on the measured signals provided by the receiver 205, a processor 206 implements the image reconstruction and various computations, and displays the reconstructed image on a CRT display unit 207. A magnetic field driver 204 generates magnetic fields necessary for the measurement based on the control signals provided by the magnetic field controller 203.

The inventive operational sequence of the foregoing arrangement will be described using FIGS. 1A, 1B, 2, 3 and 5. The control sequence of the sequence controller 201 will be described using FIG. 5.

Step 501: A region 101 is excited selectively by the 90° pulse 301 and the gradient magnetic field 303.

Step 502: A magnetic field 305 is applied in order to cancel the phase disturbance in the read-out direction.

Step 503: The direction of spins which have been excited by the 90° pulse is reversed by the 180° pulse 302 over the entire region.

Step 504: A phase-encode magnetic field 304 is applied in order to separate positions in the y-direction.

Step 505: Signals from the spins affected by both the 90° pulse 301 and 180° pulse 302 are measured while applying the magnetic field 306.

Step 506: The above steps 501–505 are repeated for a number of times necessary for imaging, while changing the phase-encoding value.

Step 507: The measured signals are transformed by using 2-dimensional Fourier transformation so that they are imaged.

Step 508: The region 103A is removed from the view field on the display when necessary for the sake of eliminating noises in the static portion in the view field 102. In this case, only the blood vessel portion 103B is displayed.

By implementing the measurement based on the above method in synchronism with the pulsation of the heart, the flow velocity can be known on the basis of the imaging position of a spin.

Figure 3:
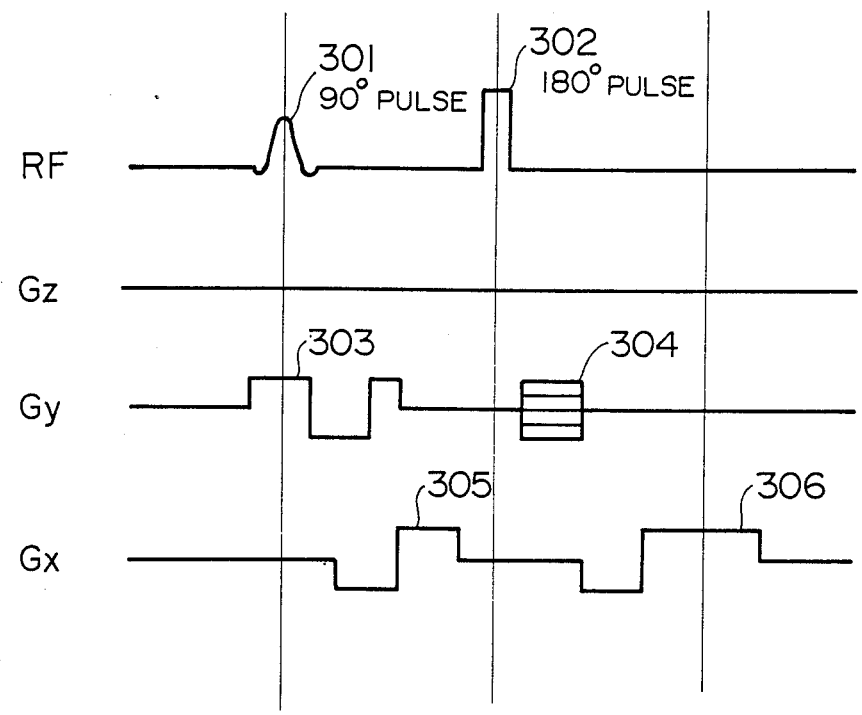
FIG. 3 is a diagram showing an embodiment of the pulse sequence for carrying out the present invention.

If the magnetic field 305 in FIG. 3 is not applied, the spin movement causes the phase to vary depending on the flow velocity in the x-direction, and hence the flow velocity can be known from the phase.

Figure 4:
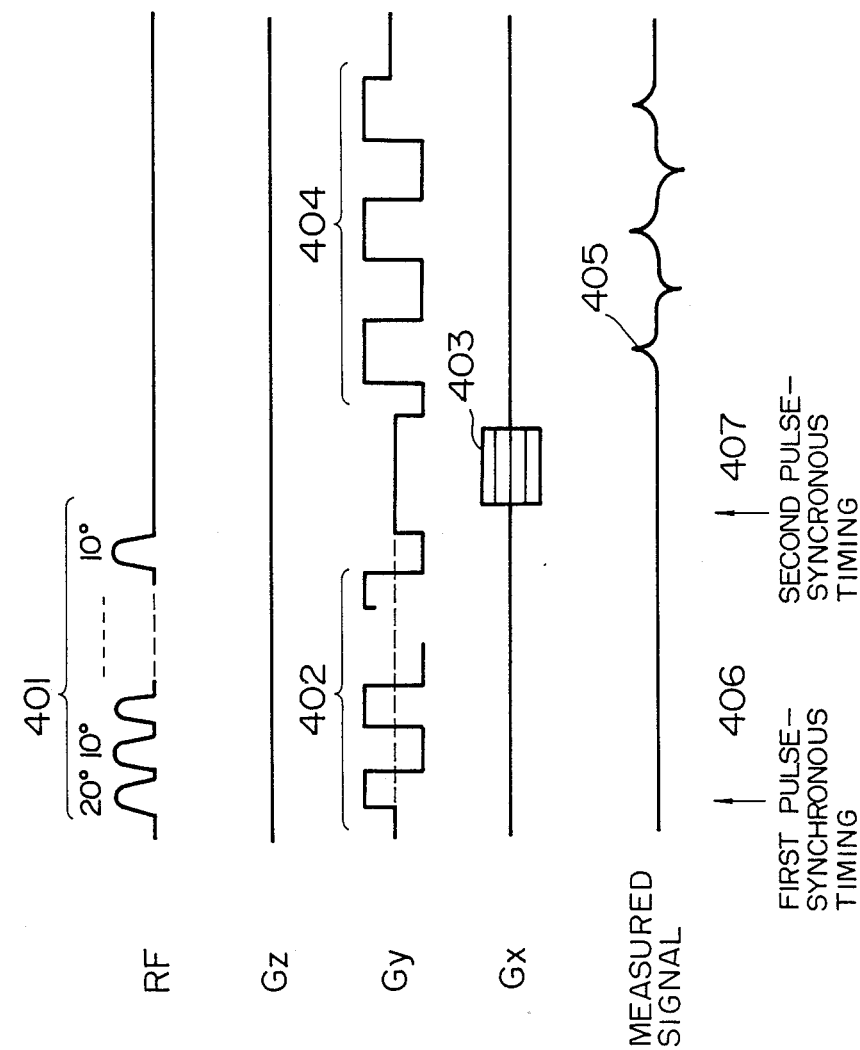
FIG. 4 is a diagram showing another embodiment of the pulse sequence.
Figure 5:
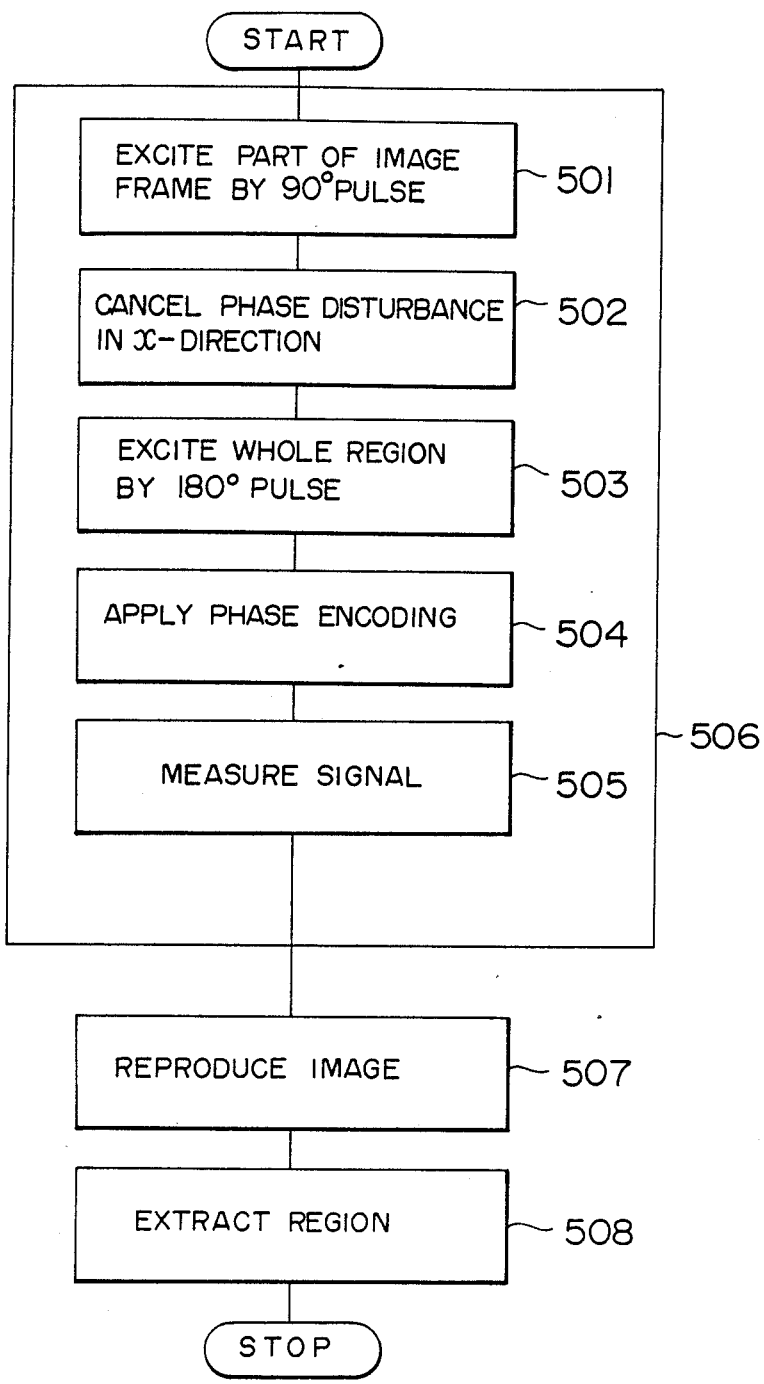
FIG. 5 is a flowchart showing the process according to an embodiment of this invention.

Described above is an example of the fundamental sequence, and FIG. 4 shows another example which is an expanded version of the above. Major alterations are the following three points.

(1) The 90° pulse 301 in FIG. 3 is replaced with consecutive pulses 401 shown in FIG. 4. The RF pulses are applied for a variable number of times in a variable applying angle in dependence on the portion to be scanned.

(2) The read-out direction is changed from x- to y-direction, and accordingly the read-out magnetic field 306 in FIG. 3 is replaced with a magnetic field 404 shown in FIG. 4.

(3) The single measurement of signal by the magnetic field 306 in FIG. 3 is expanded to multiple measurements using a magnetic field 404.

The alteration (1) provides applying of finer excitation pulses successively in place of a burst applying, enabling the interior of blood vessels to be filled with excited spins, whereby the blood vessel system can be extracted more.

Figure 1A:
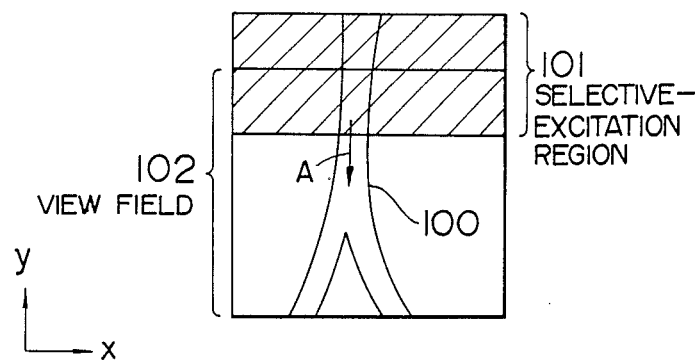
FIGS. 1A and 1B are diagrams explaining the principle of this invention for imaging only blood vessels.
Figure 1B:
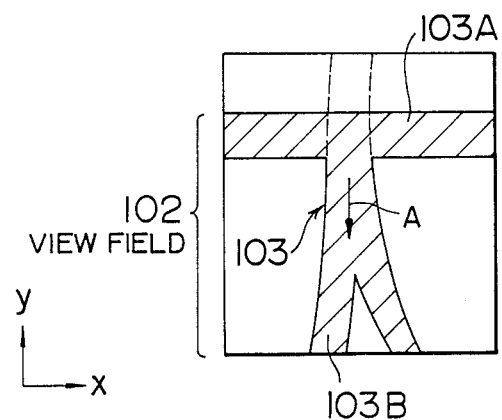

The reason for (2) is that when a selective excitation region is included in the outside of a view field in FIG. 1A, it is necessary to remove aliasing (noises generated in portions outside the view field 102 in the selective excitation region 101) in the y-direction, and this process becomes simpler by setting the read-out direction to be in the y-direction. Consequently, by putting the entirety of selective excitation region outside of the view field, it becomes possible for the sequence of FIG. 5 to easily eliminate not only the aliasing, but also the hatched portion 103A (the static part noise) at the upper part of FIG. 1B from the view field of the display.

The alteration (3) provides continuous imaging for the blood flow in a blood vessel in a multi-echo mode instead of a single echo mode, and by displaying the images, each reproduced by an echo, successively, the flow of spins can be viewed. Furthermore, by adding blood flow information reproduced from each of the echo signals of the multi-echo signal in the multi-echo mode, the imaging is improved.

There are two possible cases of synchronization with the pulsation in FIG. 4, i.e., a timing 406 before applying the RF 401, and a timing 407 before applying the phase encoding 403, and one of them can be chosen depending on the portion of image intended to be scanned and the purpose thereof. For example, when the heart is chosen for the portion, the coronary is imaged.

According to this invention, only blood vessels can be imaged through a single scanning, and therefore, the following effectiveness is presented.

(1) Time reduction for scanning.

(2) Visualization of fine blood vessels without incurring a problem of positioning error between images.

Continuous scanning in a multi-echo mode enable visualizing the movement of blood flows in a quasi-real-time sense. In addition, it is also possible to detect the flow velocity on the basis of the spin image position.

We claim:

1. A method of imaging blood flows by means of a magnetic resonance imaging apparatus which includes means for generating a static magnetic field and gradient magnetic fields, means for generating a high-frequency (RF) magnetic field, means for detecting magnetic resonance signals from a body under test, and means for implementing an image-reproducing computation on the detected signals, said method comprising the steps of:

exciting selectively a partial region of said test body including a blood vessel portion;

measuring resonance signals by utilizing spins flowing out of said excited region; and imaging a blood vessel system based on blood flow information included in the measured resonance signals, wherein said partial region is set to a region which includes a region formed by extending a view field plane and is outside of the view field.

2. A blood flow imaging method according to claim 1, wherein said measurement of resonance signals is implemented in a multi-echo mode.

3. A blood flow imaging method according to claim 2, wherein imaging is implemented by adding blood flow information reproduced from each of the signals measured in said multi-echo mode.

4. A blood flow imaging method according to claim 1, wherein said process of selective excitation includes a process of applying RF pulses successively.

5. A blood flow imaging method according to claim 4, wherein said RF pulses are applied for a variable number of times in a variable applying angle.

6. A blood flow imaging method according to claim 5, wherein said number of applying and angle of applying are varied depending on the portion to be scanned of said test body.

7. A blood flow imaging method according to claim 1, wherein said portion of selective excitation includes a part of the heart.

8. A blood flow imaging method according to claim 1, wherein said measuring process is synchronous with a pulsation of the heart.

9. A blood flow imaging method according to claim 1, wherein a flow velocity is measured on the basis of said blood flow information.

10. A method of imaging blood flows by means of a magnetic resonance imaging apparatus which includes means for generating a static magnetic field and gradient magnetic fields, means for generating a high-frequency (RF) magnetic field, means for detecting magnetic resonance signals from a body under test, and means for implementing an image-reproducing computation on the detected signals, said method comprising the steps of:

exciting selectively a partial region of said test body including a blood vessel portion;

measuring resonance signals by utilizing spins flowing out of said excited region; and imaging a blood vessel system based on blood flow information included in the measured resonance signals, wherein said spins have a major flow direction set to a phase-encode direction and said partial region is set to a region which includes a region formed by extending a view field plane and is outside of the view field.

11. A blood flow imaging method according to claim 10, wherein said process of selective excitation includes a process of applying RF pulses successively.

12. A blood flow imaging method according to claim 11, wherein said RF pulses are applied for a variable number of times in a variable applying angle.

13. A blood flow imaging method according to claim 12, wherein said number of applying and angle of applying are varied depending on the portion to be scanned of said test body.

14. A method of imaging blood flows by means of a magnetic resonance imaging apparatus which includes means for generating a static magnetic field and gradient magnetic fields, means for generating a high-frequency (RF) magnetic field, means for detecting magnetic resonance signals from a body under test, and means for implementing an image-reproducing computation on the detected signals, said method comprising the steps of:

exciting selectively a partial region of said test body including a blood vessel portion;

measuring resonance signals by utilizing spins flowing out of said excited region; and imaging a blood vessel system based on blood flow information included in the measured resonance signals, wherein said spins have a major flow direction set to a read-out direction and said partial region is set to a region which includes a region formed by extending a view field plane and is outside of the view field.

15. A blood flow imaging method according to claim 14, wherein said process of selective excitation includes a process of applying RF pulses successively.

16. A blood flow imaging method according to claim 15, wherein said RF pulses are applied for a variable number of times in a variable applying angle.

17. A blood flow imaging method according to claim 16, wherein said number of applying and angle of applying are varied depending on the portion to be scanned of said test body.

18. A blood flow imaging method according to claim 14, wherein said portion of selective excitation includes a part of the heart.

19. A blood flow imaging method according to claim 14, wherein said measuring process is synchronous with a pulsation of the heart.

20. A blood flow imaging method according to claim 14, wherein a flow velocity is measured on the basis of said blood flow information.

* * * * *